United States Patent
Ellis et al.

(10) Patent No.: US 6,416,490 B1
(45) Date of Patent: Jul. 9, 2002

(54) PMR DEVICE AND METHOD

(75) Inventors: Louis Ellis, St. Anthony; Gary L. Hendrickson, Big Lake, both of MN (US); Lauri DeVore, Seattle, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/035,736

(22) Filed: Mar. 5, 1998

Related U.S. Application Data
(60) Provisional application No. 60/064,210, filed on Nov. 4, 1997.

(51) Int. Cl.[7] .......................... A61B 17/20; A61B 18/18; A61F 7/12
(52) U.S. Cl. .......................... 604/22; 606/41; 607/113
(58) Field of Search .......................... 604/20–22, 113, 604/114, 41, 523, 264, 117, 500; 128/898; 606/27–32, 34–35, 38, 41, 45–50; 600/372–75, 394–96; 607/96–99, 104–105

(56) References Cited

U.S. PATENT DOCUMENTS

| | | | |
|---|---|---|---|
| 4,790,311 A | 12/1988 | Ruiz | |
| 4,896,671 A | 1/1990 | Cunningham et al. | |
| 5,047,026 A | 9/1991 | Rydell | 606/48 |
| 5,093,877 A | 3/1992 | Aita et al. | 385/34 |
| 5,209,749 A | 5/1993 | Buelna | 606/45 |
| 5,281,218 A * | 1/1994 | Imran | |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,431,649 A | 7/1995 | Mulier et al. | 606/41 |
| 5,522,815 A * | 6/1996 | Durgin, Jr. et al. | |
| 5,591,159 A | 1/1997 | Taheri | 606/15 |
| 5,593,405 A | 1/1997 | Osypka | 606/15 |
| 5,607,405 A | 3/1997 | Decker et al. | 604/264 |
| 5,620,414 A | 4/1997 | Campbell, Jr. | 604/22 |

(List continued on next page.)

FOREIGN PATENT DOCUMENTS

| | | |
|---|---|---|
| DE | 296 09 350 U 1 | 10/1996 |
| DE | 195 37 084 A 1 | 4/1997 |
| EP | 0 629 382 A1 | 8/1993 |
| EP | 0 807 412 A1 | 11/1997 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |

OTHER PUBLICATIONS

Mirhoseini et al., Abstract entitled "Transventricular Revascularization by Laser", *Lasers in Surgery and Medicine*, 2(2), 1982 1 page.

(List continued on next page.)

*Primary Examiner*—Angela D. Sykes
*Assistant Examiner*—P M Bianco
(74) *Attorney, Agent, or Firm*—Crompton, Seager & Tufte, LLC

(57) ABSTRACT

A catheter having an elongate shaft including a proximal and a distal end. The shaft includes a conductor. An electrode is disposed at the distal end of the shaft and is connected to the conductor. The electrode has a generally annular, cross-sectional shape. The annular shape defines an opening within the electrode. An insulator surrounds the conductor. In accordance with the method of the present invention, a crater wound can be formed through the endocardium and into the myocardium of a patient's heart. Collateral damage to the myocardium can be made by infusing pressurized fluid into the crater wound.

24 Claims, 5 Drawing Sheets

U.S. PATENT DOCUMENTS

| | | | |
|---|---|---|---|
| 5,672,174 A | 9/1997 | Gough et al. | 606/41 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 606/15 |
| 5,725,521 A | 3/1998 | Mueller | 606/7 |
| 5,725,523 A | 3/1998 | Mueller | 606/15 |
| 5,807,395 A * | 9/1998 | Mulier et al. | 606/41 |
| 5,871,469 A * | 2/1999 | Eggers et al. | 604/114 |
| 6,165,188 A * | 12/2000 | Saadat et al. | |
| 6,193,717 B1 * | 2/2001 | Ouchi | |

OTHER PUBLICATIONS

Gal et al., Abstract entitled "Analysis of Photoproducts Free Radicals and Particulate Debris Generated . . . ", *Lasers in Surgery and Medicine,* 11(2) 1991, 1 page.

Isner, J., Abstract entitled "Right Ventricular Myocardial Infarction", *JAMA,* v259, n5, Feb. 5, 1988, 12 pages.

Pickering et al., Abstract entitled "Proliferative Activity in Peripheral and Coronary Atherosclerotic Plaque . . . ", *J. Clin. Invest.,* ISSN 0021–9738, Apr. 1993, 1 page.

Vineberg et al., "Creation of Intramyocardial Pathways to Channel Oxygenated Blood Between Ventricular Arteriolar Zones", *Canad. Med. Ass. J.,* vol. 96, Feb. 4, 1967, 3 pages.

Vineberg, A. "Results of 14 Years' Experience in the Surgical Treatment of Human Coronary Artery Insufficiency", *Canad. Med. Ass. J.,* vol. 92, Feb. 13, 1965, 8 pages.

Vineberg et al., "The Ivalon Sponge Procedure for Myocardial Revascularization", *Surgery,* vol. 47, No. 2, Feb. 1960, pp. 268–289.

Vineberg et al., "Treatment of Acute Myocardial Infarction by Endocardial Resection", *Surgery,* vol. 57, No. 6, Jun. 1965, pp. 832–835.

Walter et al., "Treatment of Acute Myocardial Infarction by Transmural Blood Suply from the Ventricular Cavity", *European Surgical Research,* 3:130–138 (1971).

Khazei et al,, "Myocardial Canalization", *The Annals of Thoracic Surgery,* vol. 6, No. 2, Aug. 1968, pp. 163–171.

Hershey et al., "Transmyocardial Puncture Revascularization", *Geriatrics,* Mar. 1969, pp. 101–108.

Press Release dated Oct. 21, 1996, "Doctor's Demonstrate Proof of Blood Flow Through Open TMR Channels Created with PLC Systems . . . ", 1 page.

Press/News Release dated Oct. 10, 1996, "Texas Fieart Institute Presents Study Comparing the use of $CO_2$ . . . ", 1 page.

Goldman et al., "Nonoperative Portacaval Shunt in Swine", *Investigative Radiology,* vol. 25, No.5, May 1990, 5 pages.

* cited by examiner

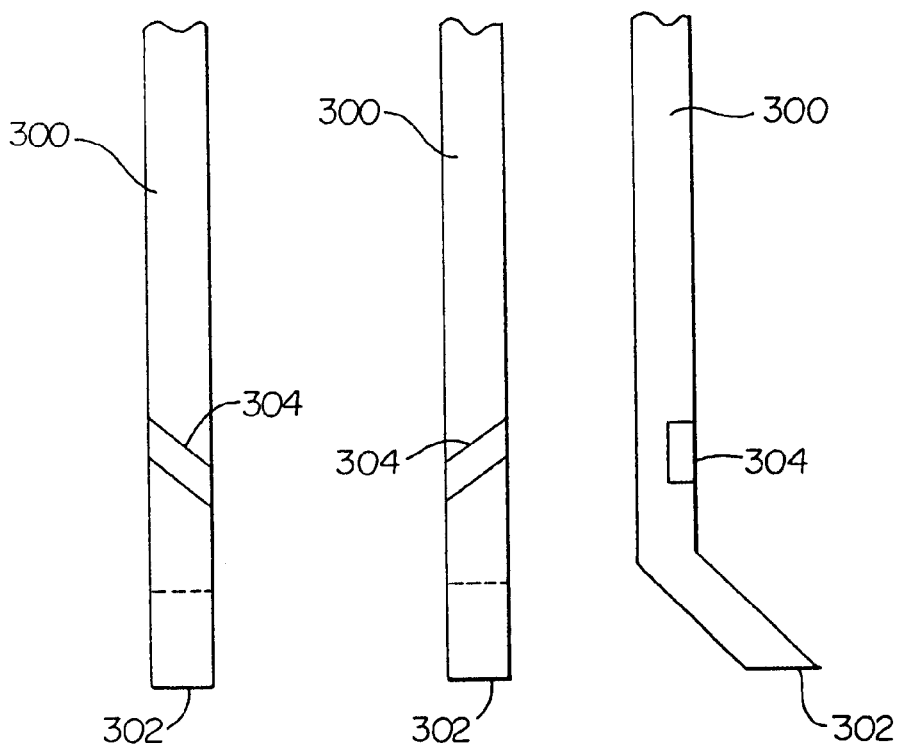
*Fig. 15*  *Fig. 16*  *Fig. 17*
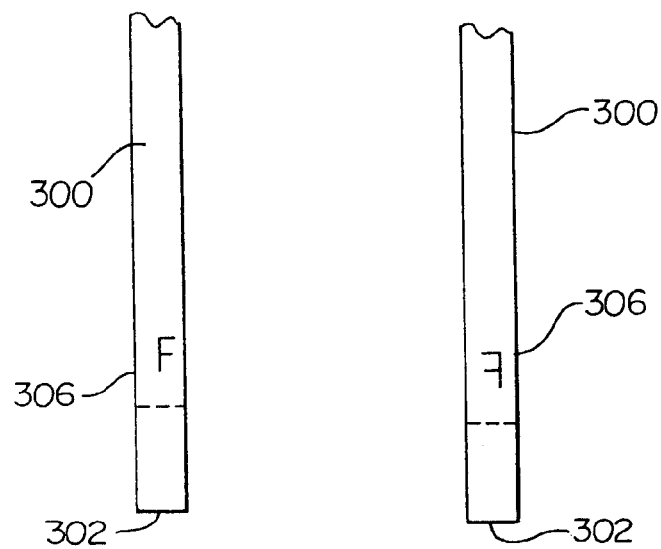
*Fig. 18*  *Fig. 19*

PMR DEVICE AND METHOD

RELATED APPLICATIONS

The present application is related to U.S. Provisional Patent Application Serial No. 60/064,210, filed on Nov. 4, 1997, and entitled TRANSMYOCARDIAL REVASCULARIZATION GROWTH FACTOR MEDIUMS AND METHOD, U.S. patent application Ser. No. 08/812,425, filed on Mar. 6, 1997, now U.S. Pat. No. 5,968,059 entitled TRANSMYOCARDIAL REVASCULARIZATION CATHETER AND METHOD, U.S. patent application Ser. No. 08/810,830, filed Mar. 6, 1997, now U.S. Pat. No. 5,938,632, entitled RADIOFREQUENCY TRANSMYOCARDIAL REVASCULARIZATION APPARATUS AND METHOD, and U.S. patent application Ser. No. 09/035,737, filed on Mar. 5, 1998, now U.S. Pat. No. 6,093,185, and entitled EXPANDABLE PMR DEVICE AND METHOD herein incorporated by reference.

FIELD OF THE INVENTION

The present invention relates generally to medical devices for forming holes in heart chamber interior walls in percutaneous myocardial revascularization (PMR) procedures. More specifically, the present invention relates to intravascular PMR devices having generally annular tips.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult. Percutaneous myocardial revascularization (PMR) has been developed as an alternative to these techniques which are directed at by-passing or removing lesions. Heart muscle may be classified as healthy, hibernating and "dead". Dead tissue is not dead but is scarred, not contracting, and no longer capable of contracting even if it were supplied adequately with blood. Hibernating tissue is not contracting muscle tissue but is capable of contracting, should it be adequately re-supplied with blood. PMR is performed by boring channels directly into the myocardium of the heart.

PMR was inspired in part by observations that reptilian hearts muscle is supplied primarily by blood perfusing directly from within heart chambers to the heart muscle. This contrasts with the human heart, which is supplied by coronary vessels receiving blood from the aorta. Positive results have been demonstrated in some human patients receiving PMR treatments. These results are believed to be caused in part by blood flowing from within a heart chamber through patent channels formed by PMR to the myocardial tissue. Suitable PMR holes have been burned by laser, cut by mechanical means, and burned by radio frequency current devices. Increased blood flow to the myocardium is also believed to be caused in part by the healing response to wound formation. Specifically, the formation of new blood vessels is believed to occur in response to the newly created wound.

SUMMARY OF THE INVENTION

The present invention pertains to a device and method for performing percutaneous myocardial revascularization (PMR). The device of the present invention can be used to form crater wounds in the myocardium of the patient's heart. A crater wound can be viewed as a wound having a width greater than its depth, whereas a channel wound is one having a depth greater than its width. A hole in the myocardium is a volumetric removal of tissue. The device can also be used to form channel wounds, but the configuration of the device's electrode(s) makes the device particularly suitable for creating crater wounds.

In the preferred form of the method in accordance with the present invention, a crater wound is made through the endocardium and into the myocardium. The wound, and thus the healing response, including angiogenisis and subsequent perfusion of tissue is enhanced by collateral damage to the myocardium. The collateral damage is preferably induced by directing pressurized saline, contrast media, drug or a combination into the crater site through the endocardium and into the myocardium. This causes the vessels, capillaries and sinuses to rupture. By creating the collateral damage, the number of wounds which need to be made during the PMR procedure can be substantially reduced as the size of each wound is increased in view of the collateral damage. Additionally, and arguably as significant as the reduction in the number of wounds which must be formed during the procedure, is the reduction of the likelihood of a myocardial perforation. This reduction is possible because the holes can be limited in depth to just through the endocardium. Once the endocardium is perforated, pressure from infused fluid can rupture the myocardial vessels without further ablation or removal of tissue.

In a preferred embodiment, a catheter in accordance with the present invention includes an elongate shaft having a proximal end and a distal end, and a conductor extending therethrough. An electrode is disposed at the distal end of the shaft and connected to the conductor. The electrode has a generally annular transverse crosssectional shape. The annular shape defines an opening within the electrode. An insulator surrounds the elongate shaft.

A stop is disposed in the opening a predetermined distance proximally of the distal end of the electrode. The shaft preferably defines a lumen in fluid communication with the opening through the electrode. In one embodiment, a needle can be disposed within the opening and be in fluid communication with the lumen to deliver contrast media, growth factors or drugs to the wound.

In another embodiment, the annular shape of the electrode is generally circular. The annular shape can be continuous or in an alternate embodiment, discontinuous and formed from a plurality of discrete electrodes positioned in an array. The electrode can also include a serrated edge that produces a plurality of electrode contact points.

A method for performing PMR in accordance with the present invention includes providing a catheter having an elongate shaft including a proximal end and a distal end. A generally annular shaped electrode is disposed at the distal end of the shaft. The electrode is advanced to proximate the endocardial surface of the myocardium of the patient's heart. The electrode is energized and advanced into the myocardium to form an annular shaped crater wound. Depth is controlled by a mechanical stop.

BRIEF DESCRIPTION OF THE DRAWINGS

FIG. 15 is a front view of a catheter electrode in accordance with the present invention;

FIG. 16 is a back view of the electrode of FIG. 14;

FIG. 17 is a side view of the electrode of FIG. 14;

FIG. 18 is a front view of yet another embodiment of an electrode in accordance with the present invention; and FIG. 19 is a back view of the electrode of FIG. 17.

DETAILED DESCRIPTION OF THE INVENTION

Figure 1:
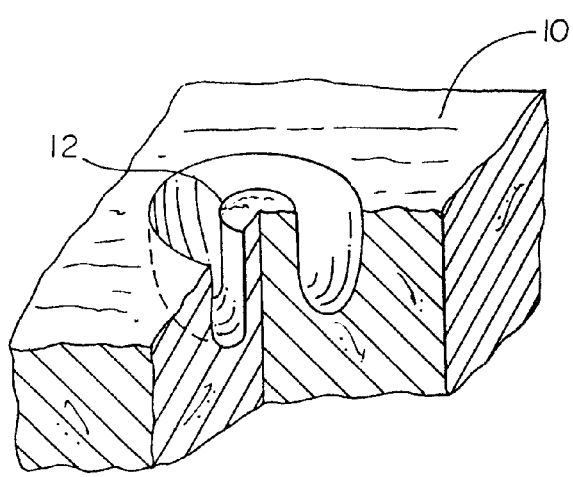
FIG. 1 is a cross-sectional, perspective view of an annular shaped crater wound in a patient's myocardium formed by a device in accordance with the present invention.
Figure 2:
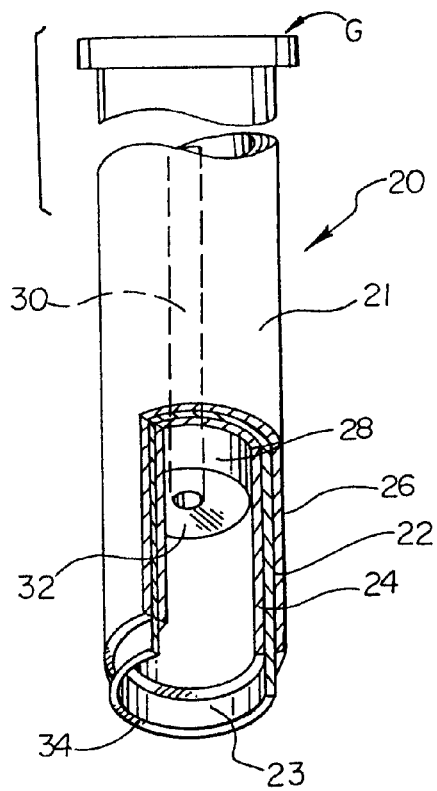
FIG. 2 is a perspective, cross-sectional view of a catheter in accordance with the present invention.

Referring now the drawings wherein like reference numerals refer to like elements through the several views, FIG. 1 is a perspective, partial cross-sectional view of a heart wall 10 having an annular hole 12 formed in the myocardium by a catheter made in accordance with the present invention. FIG. 2 is a perspective, partial crosssectional view of a catheter 20 in accordance with the present invention. Catheter 20 includes a shaft 21 having a proximal end and a distal end. Shaft 21 preferably includes an elongate hypotube sandwiched between an inner insulator 24 and an outer insulator 26. Hypotube 22 can be formed from stainless steel or Nitinol or other conductive material. It can be desirable to use a nickel-titanium alloy (for example, NITINOL™, hereafter referred to as nitinol) hypotube as the highly flexible material can act as a shock absorber while catheter 20 is pressure against the beating heart during the PMR procedure. Insulators 24 and 26 may be formed from, for example, polyethylene, polyimide or PTFE. Those skilled in the art would appreciate that other biocompatible materials can be used to form these elements. The distal end of hypotube 22 is preferably left uninsulated to form an annularly-shaped electrode 23.

A stop 28 is preferably disposed within shaft 21. Stop 28 preferably defines a lumen 30 extending therethrough. Stop 28 includes a distal end 32 spaced a predetermined distance from a distal end 34 of electrode 23. This predetermined distance can be used to control the depth of holes 12 formed in the myocardium of a patient's heart. Those skilled in the art will recognize the non-conductive, biocompatible materials available to form stop 28, for example PEPI.

In view of the discussion below regarding the use of catheter 20, those skilled in the art of catheter construction would recognize the various possibilities for manifolds to be disposed at the proximal end of catheter 20, and that a suitable radio frequency (RF) generator G can be conductively connected to hypotube 22 to deliver RF energy to electrode 23.

Figure 3:
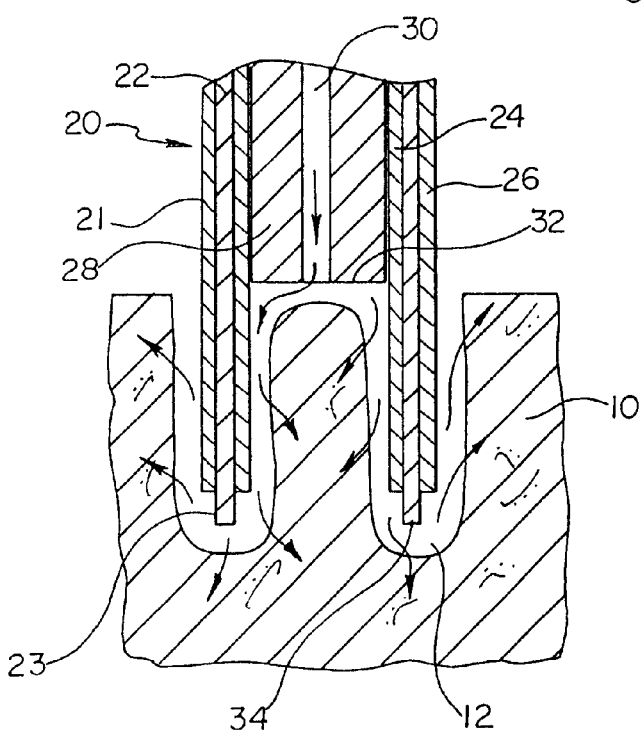
FIG. 3 is a cross-sectional view of the catheter of FIG. 2 in use.

FIG. 3 is a cross-sectional view of catheter 20 in use. In FIG. 3, electrode 23 has been energized with RF energy and advanced into heart wall 10 to form hole 12. As shown by the arrows, contrast medium, growth factor or other drugs are being infused through lumen 30 into hole 12, and then into myocardium 10. It can be noted that in FIG. 3 that distal end 32 of stop 28 is spaced a predetermined distance from distal end 34 of electrode 23 such that the depth of hole 12 is approximately equal to its width. The predetermined distance can be varied such that shallower holes or craters are formed, or alternatively the distance can be increased to form channels.

Figure 4:
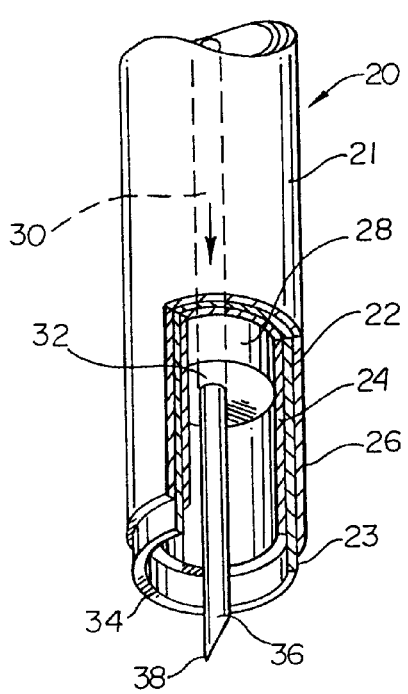
FIG. 4 is a perspective, cross-sectional view of an alternate embodiment of the catheter in accordance with the present invention.

FIG. 4 is a perspective, partial cross-sectional view of catheter 20 modified to include a hypotube or needle 36 extending distally from lumen 30. The distal end of hypotube 36 includes a sharpened end 38, and a lumen defined therethrough in fluid communication with lumen 30. Hypotube 36 can also act as a bi-polar ground.

Figure 5:
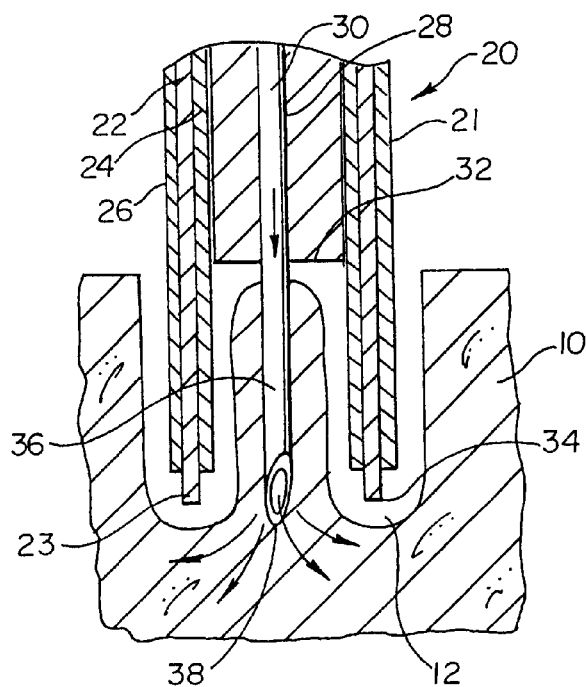
FIG. 5 is a cross-sectional view of the catheter of FIG. 4 in use.

FIG. 5 is a cross-sectional view of catheter 20 including hypotube 36. This view is similar to that of FIG. 3, except that rather than infusion fluid into hole 12, as shown by the arrows, fluid is directed into the myocardium.

Figure 6:
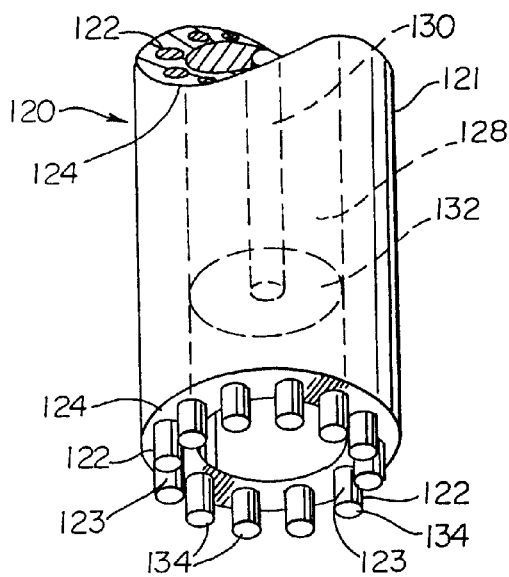
FIG. 6 is a perspective view of the distal end of yet another alternate embodiment of a catheter in accordance with the present invention.

FIG. 6 is an alternate embodiment of a catheter 120 in accordance with the present invention. Many elements of catheter 120 are similar to that of catheter 20 as shown in FIG. 2. Rather than shaft 121 including a hypotube 22, shaft 121 includes a plurality of elongate conductive members 122 embedded in a tubular insulator 124. A distal portion of members 122 is preferably left uninsulated to form a generally annularly shaped array of electrodes 123. One or more of electrodes 123 may comprise a needle. A stop 128 is disposed within tubular member 124. Stop 128 defines a lumen 130 extending therethrough. Stop 128 includes distal end 132 spaced a predetermined distance proximally of distal ends 134 at electrodes 123 to control the depth of the holes created by catheter 123. I can be appreciated by those skilled in the art that catheter 120 can be used in substantially the same manner to perform PMR as catheter 20 shown in FIG. 3. A plurality of electrodes, having a surface area less than a continuous annular electrode requires less energy to arc or ablate. A plurality of electrodes will also tend to grab tissue, stabilizing the electrode on a moving heart wall.

Figure 7:
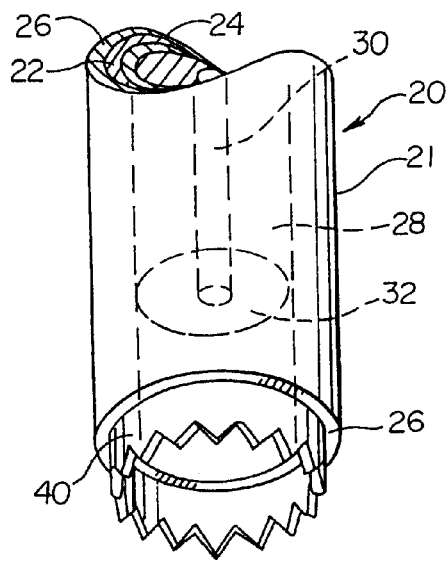
FIG. 7 is a perspective view of yet another alternate embodiment of the catheter in accordance with the present invention.

FIG. 7 is a perspective view of a modified embodiment of catheter 20 of FIG. 2. In particular, the distal end of hypotube 22 has been serrated to form a serrated electrode 40. Serrating electrode 40 changes the surface of the electrode contacting the tissue and thus reduces the power needed to arc. Serrated electrode 40 will also grab tissue, securing electrode 40 to a moving heart wall during crater formation.

Figure 8:
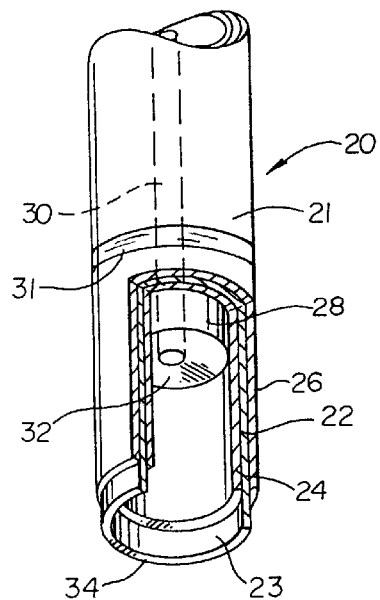
FIG. 8 is a perspective view of yet another alternate embodiment of the catheter in accordance with the present invention.

FIG. 8 is a view of yet another embodiment of catheter 20 in accordance with the present invention. To catheter 20 has been added a second grounded or return electrode 31 to form a bi-polar RF PMR catheter. It can be appreciated that this electrode can also be added to catheter 120 of FIG. 6 and catheter 20 of FIG. 7 to make each of these embodiments bi-polar as well.

Figure 9:
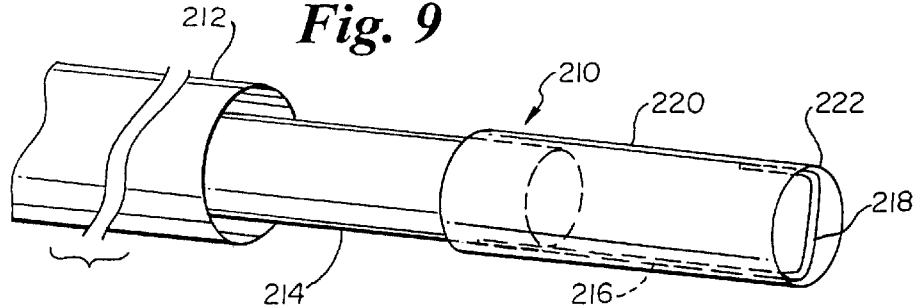
FIG. 9 is a perspective view of yet another alternate embodiment of the catheter in accordance with the present invention.

FIG. 9 is a perspective view of yet another embodiment of a catheter 210 in accordance with the present invention disposed within a guide catheter 212. Catheter 210 includes an elongate shaft 214. Elongate shaft 214 is preferably formed from an elongate tubular, and conductive member such as a stainless steel or Nitinol hypotube. Shaft 214 defines an infusion lumen therethrough. The wall of the lumen and the exterior shaft 214 are preferably insulated, by a layer of, for example, polyethylene. An electrode 216 is connected to shaft 214 by solder or another conductive connection.

Electrode 216 can be formed from a wire or ribbon shaped member which extends distally from shaft 214 to a generally linearly and transversely extending distal end 218. All but distal end 218 of electrode 216 can be insulated with, for example, PTFE to focus RF energy at end 218. Electrode 216 can be partially or completely surrounded by a hood 220 extending from shaft 214. Hood 220 preferably defines an infusion lumen in fluid communication with the infusion lumen of shaft 214. All or a portion of electrode 216 can be disposed in the infusion lumen. Hood 220 includes a distal end 222. Distal end 218 could be plated with gold or other radiopaque material to act as a marker.

Figure 10:
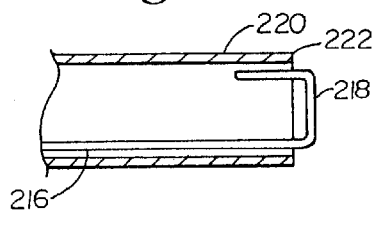
FIG. 10 is a cross-sectional view of the catheter of FIG. 8.
Figure 11:
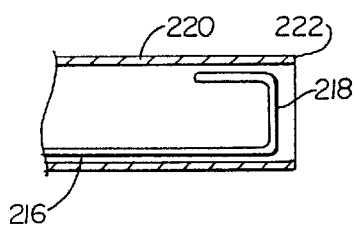
FIG. 11 is a cross-sectional view of the catheter of FIG. 8.
Figure 12:
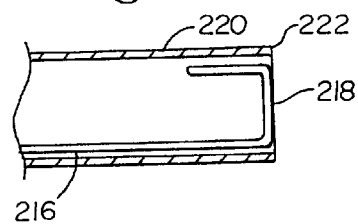
FIG. 12 is a cross-sectional view of the catheter of FIG. 8.

FIG. 10 is a cross-sectional view of hood 220 showing electrode 218 extending distally beyond distal end 222. By contrast, in FIG. 11, electrode 216 is entirely disposed proximally of end 222. In FIG. 12, distal end 218 of electrode 216 is disposed flush with end 222 of hood 220. The relative positioning of hood 220 and electrode 216 can have an effect on the depth of craters formed by catheter 210, as explained in more detail below.

Figure 13:
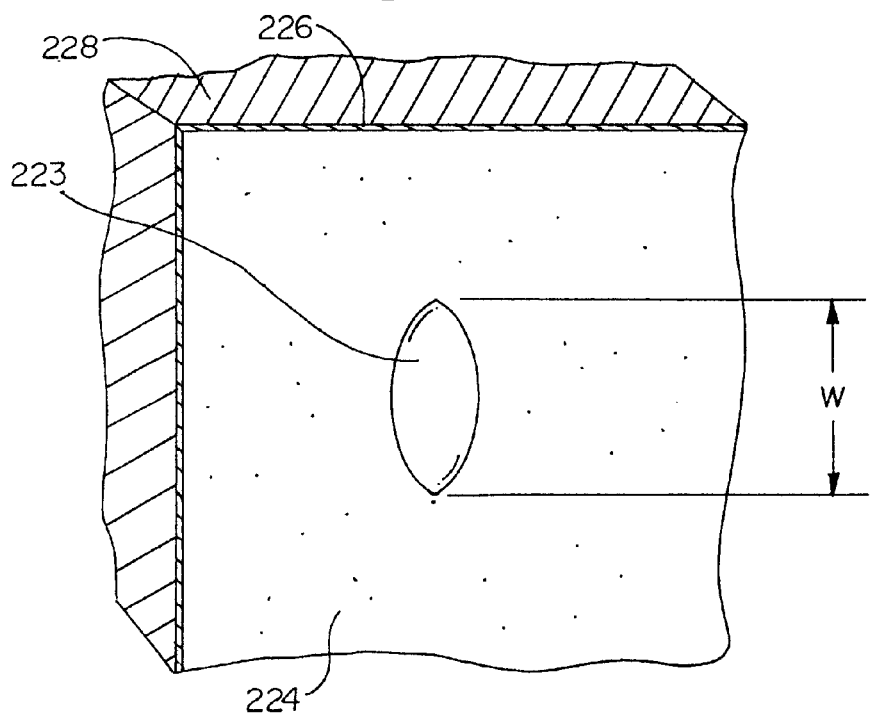
FIG. 13 is a top view of a crater formed in the endocardium.
Figure 14:
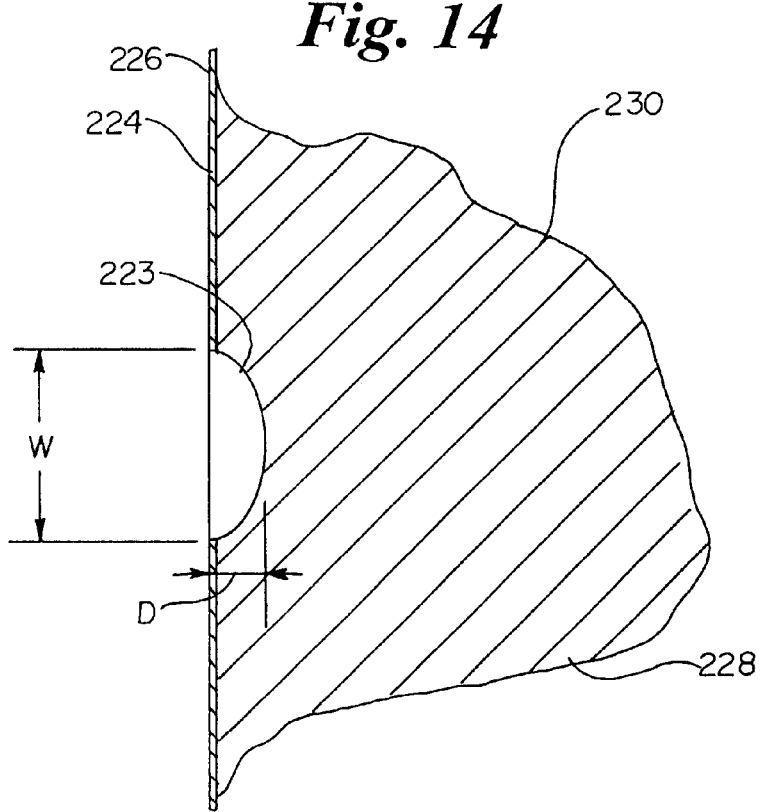
FIG. 14 is a cross-sectional view of the crater of FIG. 12.

FIG. 13 is a view directly into a crater 223 formed by a typical electrode 218 viewed from a perspective perpendicular to a surface 224 of endocardium 226. Crater 223 extends into myocardium 228 of a patient's heart. FIG. 14 is a cross-sectional view of crater 223 of FIG. 13.

The depth D of crater 223 is a function of the power delivered to electrode 216 and the relative position of the electrode 216 to distal end 222 of hood 220. The more power delivered to electrode 216, the greater the depth of crater 223. With respect to the position of electrode 216 relative to hood 220, the position of electrode distal end 218 relative hood distal end 222 of FIG. 10 creates the deepest crater. The positioning shown in FIG. 11 would create the shallowest, whereas the positioning of FIG. 12 would create a crater of intermediate depth.

The width W of crater 223 is a function of the transverse extent of distal end 218 of electrode 216, and the power delivered to the electrode. The greater the transverse extent of distal end 218, the greater the width of crater 223. The more power that is delivered to electrode 216, the wider will be crater 223.

In use, catheter 210 is preferably advanced percutaneous to the endocardium of a patient's heart. This route will normally be by way of the femoral artery and the aorta to the left ventricle. Distal end 222 is brought into contact with the endocardium, preferably, such that the perimeter of distal end 222 is entirely in contact with the endocardium. Electrode 216 disposed in one of the positions shown in FIGS. 10–12, is energized to form a crater. A fluid under pressure is then forced into the crater by way of the infusion lumen through shaft 214 and hood 220. This fluid can be saline, contrast media, a drug or any combination of these. By forcing fluid under pressure into the myocardium, the vessels, capillaries, and sinuses will be collaterally damaged within an area 230 about crater 223. This will increase the healing response by angiogenisis associated with the crater. The likelihood of perforating the myocardium is reduced as the depth of the crater need only be sufficient to penetrate the endocardium.

The following are exemplary technical specifications for catheter 210 as configured in FIG. 12:

A. Output power vs. impedance specifications-channel or crater making PMR device;
  1. Output power vs. impedance is preferably flat across a wide range of impedance values for desired therapeutic power level.
  2. Exemplary power requirements: a) output power approximately 30–40 watts into 100 to 10,000 ohms; b) output voltage approximately 1,200 to 2,000 V P-P into approximately 100 to 10,000 ohms; c) output current approximately 100 to 300 ma P-P into about 100 to 10,000 ohms voltage is preferably large enough to sustain cutting effect for a given electrode while delivery current as low as possible.

B. The RF wave form is preferably 500 KHz or higher unmodulated continuous sine wave.

C. The delivery type can be mono-polar delivery with small area dispersive electrode for lower power applications.

D. RF delivery control.
  1. Preferably fixed power to provide cutting effect.
  2. Delivery controlled by application timer preferably fixed at about 0.6 to 1.0 seconds.

It can be appreciated, that angiogenisis is also stimulated by the thermal injury creating the crater, and fluid pressure entering the myocardium from the left ventricle through the endocardium by way of the crater. Hemorrhaging of the subendocardial vasculature may also occur in response to adjacent tissue ruptures or ablation.

FIG. 15 is a front view of an elongate electrode 300 having an angled distal end 302. Disposed on the front of electrode 300 is an asymmetrical radiopaque marker 304. Marker 304 could be formed from, for example, gold or platinum. As electrode 300 is rotated 180° around its longitudinal axis, electrode 300 will appear as shown in FIG. 16. FIG. 16 is a fluoroscopic back side view of electrode 300 wherein marker 304 appears in mirror image to its position FIG. 15.

FIG. 17 is a side view of electrode 300 rotated 90° round about its longitudinal axis relative to its position in FIG. 15. It can be appreciated that by providing an asymmetrical marker band, the relative rotational position of the catheter or electrode in a patient can be determined by fluoroscopy.

FIGS. 18 and 19 are views of the front and back, respectively of electrode 300 including an alternate marker 306 configured as an F. It can be appreciated that various asymmetrical marker configurations can be used in accordance with the present invention.

It is noted several times above that contrast media can be infused into the holes, craters, wounds, or channels formed during a PMR procedure. Normal contrast media formulations will tend to dissipate rapidly into the patient's blood stream as the patient's heart continues to beat. In order to retain the contrast media within the crater for an extended period of time, a mixture of 498 Loctite™ adhesive can be radiopaque loaded with platinum or other biocompatible radiopaque material to a weight percentage sufficient to be visible under fluoroscopy.

In use, the catheters of the present invention can be advanced percutaneously to a chamber of a patient's heart, for example, the left ventricle. The percutaneous route for advancement will generally be by way of the femoral artery and the aorta. The electrode is then brought into close proximity with the chamber wall. The electrode is energized and repeatedly plunged into the myocardium to form a plurality of holes.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A catheter assembly, comprising:
   an elongate shaft having a proximal end and a distal end, and including a conductor;
   an electrode disposed at the distal end of the shaft and connected to the conductor, the electrode having a generally annular transverse cross-sectional shape, the annular shape defining an opening within the electrode, the electrode having a distal end;
   a stop disposed in the opening proximally a distance from the distal end of the electrode;
   an insulator surrounding the conductor wherein the shaft defines a lumen in fluid communication with the opening and a needle is disposed within the opening in fluid communication with the lumen; and
   wherein the needle has an outside diameter and the opening has an inside diameter and wherein the outside diameter of the needle is substantially smaller than the inside diameter of the opening so that tissue may be disposed within the opening between the needle and the electrode.

2. A catheter assembly in accordance with claim 1, wherein the stop is disposed in the opening proximally a predetermined distance from the distal end of the electrode.

3. A catheter assembly in accordance with claim 1, wherein the insulator includes polyethylene.

4. A catheter assembly in accordance with claim 1, wherein the insulator includes polyimide.

5. A catheter assembly in accordance with claim 1, wherein the shaft includes a stainless steel hypotube.

6. A catheter assembly in accordance with claim 1, wherein the shaft includes a nickel-titanium alloy hypotube.

7. A catheter assembly in accordance with claim 1, further comprising a radiofrequency generator connected to the conductor.

8. A catheter assembly in accordance with claim 1, wherein the annular shape is generally circular.

9. A catheter assembly in accordance with claim 1, wherein the annular shape is continuous.

10. A catheter assembly in accordance with claim 1, wherein the annular shape is discontinuous.

11. A catheter assembly in accordance with claim 10, wherein the annular shape is formed by a plurality of electrodes positioned in an array.

12. A catheter assembly in accordance with claim 1, wherein the electrode includes a plurality of distally projecting members.

13. A catheter assembly in accordance with claim 12, wherein the electrode is serrated to grab tissue.

14. A catheter assembly in accordance with claim 1, further comprising a second electrode.

15. A catheter assembly in accordance with claim 14, wherein the electrode comprises a needle.

16. A catheter assembly in accordance with claim 1, wherein the stop is non-conductive.

17. A catheter assembly, comprising:
    an elongate shaft having a proximal end and a distal end, and including a conductor;
    an electrode disposed at the distal end of the shaft and connected to the conductor, the electrode having a generally annular transverse cross-sectional shape, the annular shape defining an opening within the electrode, the electrode having a distal end;
    a stop disposed in the opening proximally a distance from the distal end of the electrode;
    an insulator surrounding the conductor wherein the shaft defines a lumen in fluid communication with the opening and a needle is disposed within the opening in fluid communication with the lumen; and
    wherein the needle has an outside diameter and the opening has an inside diameter and wherein the outside diameter of the needle is about one-half or smaller than the inside diameter of the opening.

18. A method of performing PMR, comprising the steps of:
    providing a catheter assembly including an elongate shaft having a proximal end and a distal end, and including a conductor; an electrode disposed at the distal end of the shaft and connected to the conductor, the electrode having a generally annular transverse cross-sectional shape, the annular shape defining an opening within the electrode, the electrode having a distal end; a stop disposed in the opening proximally a distance from the distal end of the electrode; an insulator surrounding the conductor wherein the shaft defines a lumen in fluid communication with the opening and a needle is disposed within the opening in fluid communication with the lumen; and wherein the needle has an outside diameter and the opening has an inside diameter and wherein the outside diameter of the needle is substantially smaller than the inside diameter of the opening so that tissue may be disposed within the opening between the needle and the electrode;
    advancing the catheter assembly to a location proximate a wall of a patient's heart;
    energizing the electrode; and
    advancing the electrode into the wall of the patient's heart.

19. The method in accordance with claim 18, wherein the step of advancing the electrode into the wall of the patient's heart includes forming a hole having a depth defined by the distance between the distal end of the electrode and the stop.

20. The method in accordance with claim 18, wherein the step of advancing the electrode into the wall of the patient's heart includes contacting the stop with the wall of the patient's heart.

21. The method in accordance with claim 18, wherein the step of advancing the electrode into the wall of the patient's heart includes disposing at least a portion of the wall of the patient's heart within the opening between the needle and the electrode.

22. The method in accordance with claim 18, further comprising the step of delivering saline through the needle.

23. The method in accordance with claim 18, further comprising the step of delivering a drug through the needle.

24. The method in accordance with claim 18, further comprising the step of infusing fluid into the wall of the patient's heart through the needle.

* * * * *